United States Patent [19]

Kraus

[11] Patent Number: 5,466,799
[45] Date of Patent: Nov. 14, 1995

[54] SYNTHESIS OF BENZODIAZEPINES

[75] Inventor: George A. Kraus, Ames, Iowa

[73] Assignee: Iowa State University Research Foundation, Inc., Ames, Iowa

[21] Appl. No.: 286,929

[22] Filed: Aug. 8, 1994

[51] Int. Cl.⁶ .................... C07D 243/20; C07D 243/16
[52] U.S. Cl. .................... 540/573; 540/569; 540/574
[58] Field of Search .................... 540/515, 512, 540/514, 569, 573, 574

[56] References Cited

U.S. PATENT DOCUMENTS

| | | | |
|---|---|---|---|
| 3,109,843 | 11/1963 | Reeder et al. | 260/239 |
| 3,136,815 | 6/1964 | Reeder et al. | 260/562 |
| 3,313,815 | 4/1967 | Wolfe et al. | 260/256.4 |
| 3,371,085 | 2/1968 | Reeder et al. | 260/239.3 |
| 4,335,054 | 6/1982 | Blaser et al. | 260/465 G |
| 5,089,273 | 2/1992 | Rinehart et al. | 424/520 |
| 5,256,663 | 10/1993 | Rinehart et al. | 514/250 |

OTHER PUBLICATIONS

Farina, V. et al. "Palladium Catalysis in Cephalosporin Chemistry: General Methodology for the Syntheis of Cephem Side Chains". *J. Org. Chem.* 55, 5833–5847 (1990).
Wickham, P. P. et al. "Benzyne Generation from Aryl Triflates." *J. Org. Chem.* 56, 2045–2050 (1991).
Katmizky, A. R. et al. *Handbook of Heterocyclic Chemistry* (Pergamon Press, New York), p. 476 (1985).
Echavarren, A. M. et al. "Palladium–Catalyzed Coupling of Aryl Triflates with Organostannemes." *J. Am. Chem. Soc.* 109, 5478–5486 (1987).
Dolle, R. E. et al., "Palladium Catalyzed Alkoxycarbonylation of Phenols to Benzoate Esters." *J. Chem. Soc., Chem. Commun.* (12), 904–905 (1987).
G. T. Crisp et al., "Palladium–Catalyzed Carbonylative Coupling of Vinyl Triflates with Organostannaes. A Total Synthesis of $(\pm)^{9(12)}$–Capnellene", *J. Am. Chem. Soc.*, 106, 7500–7506 (1984)***.
A. M. Felix et al., "Quinazolines and 1,4–Benzodiazepines. SLIII (1). Oxidations with Ruthenium Tetroxide", *J. Het. Chem.*, 5, 731–734 (Oct. 1968).
M. Gates, "New Synthesis of Diazepam", *J. Org. Chem.*, 45, 1675–1681 (1980).
M. Gerecke, "Chemical Structure and Properties of Midazolam Compared with other Benzodiazepines", *Brit. J. Clin. Pharmacol.*, 16, 11S–16S (1983).
T. A. Hamor et al., "The Benzodiazepines"]in *Progress in Med. Chem.*—vol. 20; G. P. Ellis et al., Eds.; Elsevier Science Publishers: Amsterdam; pp. 157–223 (1983).
M. Ishikura et al., "New Synthesis of Diazepam and the Related 1,4–Benzodiazepines by means of Palladium–Catalyzed Carbonylation", *J. Org. Chem.*, 47, 2456–2461 (1982).
G. A. Kraus et al., "Quinone Photochemistry. A General Synthesis of Acylhydroquinones", *J. Org. Chem.*, 57, 3256–3257 (1992).
J. E. McMurry et al., "A New Method of Olefin Synthesis. Coupling of Lithium Dialkylcuprates with Enol Triflates", *Tetrahedron Letters*, 21, 4313–4316 (1980).
J. E. McMurry et al., "A Method for the Regiospecific Synthesis of Enol Triflates by Enolate Trapping", *Tetrahedron Letters*, 24, 979–982 (1983).
W. Milkowski et al., "1,4–Benzodiazepines and 1,5–benzodiazocines. VII. Synthesis and biological activity", *Eur. J. Med. Chem.—Chim. Ther.*, 20, 345–358 (1985).
W. J. Scott et al., "Palladium–Catalyzed Coupling of Vinyl Triflates with Organostannanes. A Short Synthesis of Pleraplysillin–1", *J. Am. Chem. Soc.*, 106, 4630–4632 (1984).
L. H. Sternbach et al., "Quinazolines and 1,4–Benzodiazepines. IV. Tranformations of 7–Chloro–2–methylamino–5–phenyl–3H–1, 4–benzodiazepine 4–Oxide", *J. Org. Chem.*, 26, 4936–4941 (Dec. 1961).
L. H. Sternbach et al., "Quinazolines and Benzodiazepines. XV. 7–Nitro–and 7–Trifluoromethyl–2, 3–dihydro–5–phenyl–1H–1,4–1,4–benzodiazepines and Their Tranformations", *J. Org. Chem.*, 28, 3013–3016 (Nov. 1963).

*Primary Examiner*—Mukund J. Shah
*Assistant Examiner*—King L. Wong
*Attorney, Agent, or Firm*—Schwegman, Lundberg & Woessner

[57] ABSTRACT

A general method is provided for the synthesis of substituted 2,3-dihydro-5-phenyl-1H-1,4-benzodiazepines by the reaction of bis-trifiated-2,5-dihydroxy benzophenones with 1,2-bisaminoethanes, followed by displacement of the 7-trifloxy group.

8 Claims, No Drawings

SYNTHESIS OF BENZODIAZEPINES

BACKGROUND OF THE INVENTION

This invention was made with Government grant support under NSF Grant No. CHE-9310097 and EPA Grant No. R820558-01-0. The U.S. Government has certain rights in the invention.

Since thee appearance in 1959, the 1,4-benzodiazepines have been an important class of compounds in medicinal chemistry. A remarkable variety of these compounds has been extensively investigated as psychotropic agents. See, for example, T. A. Hamor et al., eds., in *Progress in Med. Chem.*, G. P. Ellis et al., eds., *Elsevier Science Publ.*, 20, 157 (1983). Among other properties, their anxiety relieving effects are widely used in clinical practice, and the expression "benzodiazepines" has become almost synonymous with anxiolytics. See, M. Gerecke, *Brit. J. Clin. Pharmacol.*, 16, 11 (1983). The best known benzodiazepine is, of course, diazepam (7-chloro-1,3-dihydro-1-methyl-5-phenyl- 2H-1, 4-benzodiazepin-2-one) or "Valium":

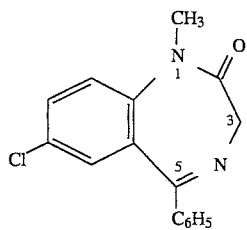

which was patented by Hoffman-La Roche, Inc. in 1968 and, in the recent past, has been the most widely-prescribed drug in the world. See, Reeder et al. (U.S. Pat. No. 3,371,085). However, many other 5-aryl-3H-1,4-benzodiazepin-2(1H)-ones have been synthesized and evaluated for pharmacological activity. For example, *The Merck Index* (11 th ed. 1989) lists at least eleven other bioactive benzodiazepines, which vary from diazepam primarily in the substiments present on the aromatic rings and at the saturated amine. As noted by W. Milkowski et al., *Eur. J. Med. Chem.—Clin. Ther.*, 20, 345 (1985), some unexpected pharmacological activities have been reported for these compounds, including antagonistic activity for flumazepil (Ro 15-1788), antidepressant activity for adinazolam, opioid activity for tifluadom and inducing sleep for flurazepam and temazepam.

Although 5-phenyl-3H-1,4-benzodiazepin-2-(1H)-one can be prepared from 2-aminobenzophenone and glycine ether ester hydrochloride in one step, the synthesis of ring-substituted benzodiazepines requires the use of bis-substituted benzophenones, such as 2-amino-5-chlorobenzophenone, that are both more difficult to obtain and to manipulate. See, for example, U.S. Pat. No. 3,313,815. Thus, a need exists for new syntheses of benzodiazepines that can be readily adapted to the synthesis of a variety of known and novel diazepam analogs.

SUMMARY OF THE INVENTION

The present invention provides a synthesis of 2,3-dihydro-5-phenyl-1H-1,4-benzodiazepines of general formula (I):

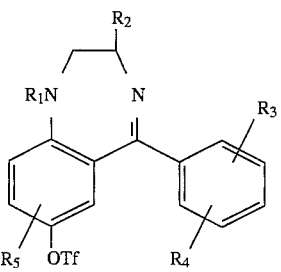

wherein $R_1$ is H or $(C_1-C_4)$alkyl, optionally substituted by $CF_3$ or $N(R)_2$ wherein each R is individually H, phenyl, or $(C_1-C_4)$alkyl; $R_2$ is H, $(C_1-C_4)$alkyl optionally substituted by $(C_1-C_4)$alkoxyl, $(C_1-C_4)$alkoxycarbonyl, phenyl, or OY, wherein Y is $(C_1-C_4)$alkyl or an acid labile protecting group, $R_3$, $R_4$ and $R_5$ are individually H, halo (Br, Cl, F, I), $(C_1-C_4)$alkoxy, nitro, $CF_3$ or $OCF_3$, and Tf is trifluoromethylsulfonyl; comprising the steps of reacting a 2,5-dihydroxybenzophenone of general formula (II):

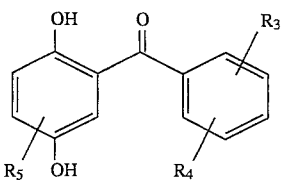

wherein $R_3$, $R_4$ and $R_5$ are as defined above, with a triflating reagent to yield a compound of formula (III):

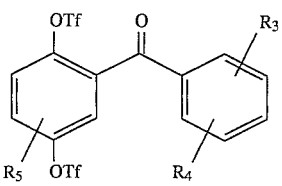

wherein $R_3$, $R_4$, $R_5$ and Tf are as defined above; followed by reaction of compound III with a 1,2-bisaminoethane of formula (IV): $(R_1)(H)NCH_2CH(R_2)NH_2$ to yield the compound of formula I, wherein $R_1$, $R_2$, $R_3$, $R_4$, and $R_5$ and Tf are as defined above. Compound (I) is a versatile intermediate that can readily be converted to compounds of formula V:

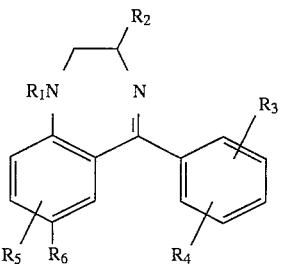

wherein $R_6$ is OH; halo, nitro, $(C_1-C_4)$alkoxy, CN, $CF_3$, $OCF_3$, CN, carboxyl, or $(C_1-C_4)$alkylO$_2$C and the like, by one- or two-step procedures that are known to the art involving the Pd-catalyzed cleavage of the Ar-OTf bond. For example, medazepam (V, $R_1=CH_3$, $R_2=R_3=R_4=R_5=H$, $R_6=Cl$ can readily be prepared from the corresponding compound (I) by displacement of OTf by chloride anion in the presence of a palladium catalyst. In turn, medazepam can readily be converted to diazepam under known oxidation conditions. Similar palladium catalyzed reactions can readily yield compounds of formula V wherein $R_6$ is CN or $CO_2CH_3$, as shown in Scheme I, below, for compounds 3-6.

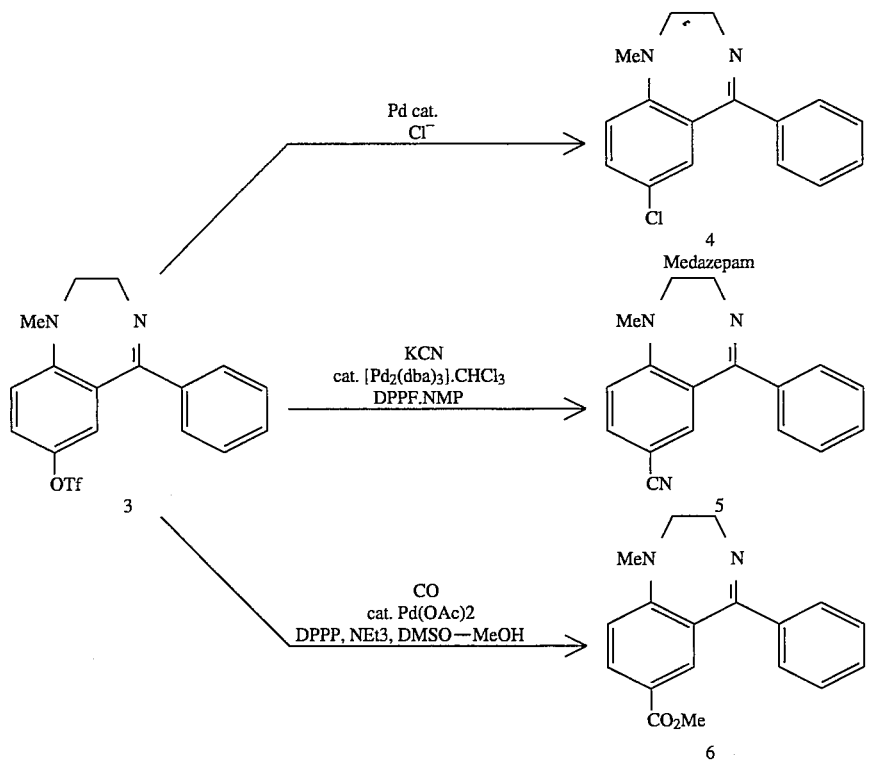

Likewise, starting dihydroxybenzophenone (II) can be readily prepared by the photochemical alpha-addition of a benzaldehyde of formula $(R_3)(R_4)ArCHO$ to a 3,5-, 3,6- or 5,6-disubstituted quinone, by the general procedure of A. M. Felix et al., *J. Heterocycl. Chem.*, 5, 731 (1968).

DETAILED DESCRIPTION OF THE INVENTION

Representative diazepam analogs of formula VI, that can be prepared in accord with the invention by oxidizing compound V, and optionally converting OY to OH, are summarized on Table I, below:

TABLE I

Benzodiazepines (VI)

| Compound | $R_1$ | $R_2$ | $R_3$ | $R_4$ | $R_5$ | $R_6$ |
|---|---|---|---|---|---|---|
| Flurazepam | $(Et)_2NCH_2CH_2$ | H | 2'-F | H | H | Cl |

TABLE I-continued

Benzodiazepines

| | | | | | |
|---|---|---|---|---|---|
| Halazepam | $F_3CCH_2$ | H | H | H | H | Cl |
| Lorazepam | H | OH | 2'-Cl | H | H | Cl |
| Prazepam | $cC_3H_5$ | H | H | H | H | Cl |
| Oxazepam | H | OH | H | H | H | Cl |
| Temazepam | $CH_3$ | OH | H | H | H | Cl |
| Flunitrazepam | $CH_3$ | H | 2'-F | H | H | $NO_2$ |
| Flutoprazepam | $xC_3H_5$ | H | 2'-F | H | H | Cl |
| Nordazepan | H | H | H | H | H | Cl |
| Diazepam | $CH_3$ | H | H | H | H | Cl |

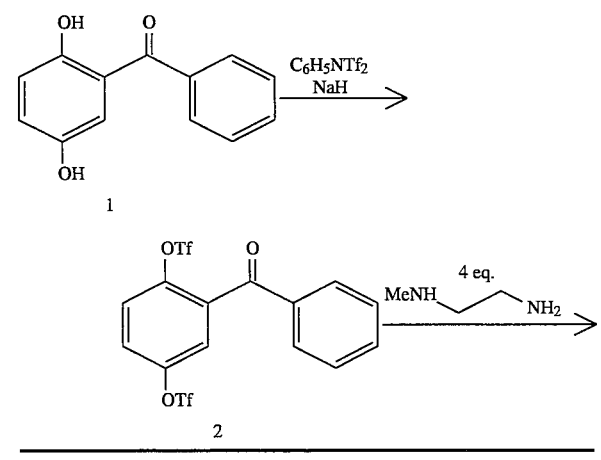

For example, compound 3 can be prepared from 2,5-dihydroxybenzophenone (1) as shown in Scheme 2.

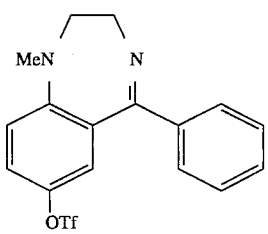

Compounds of formula 1, comprising substituents $R_3$-$R_6$, can be readily prepared by the photochemical reaction of benzaldehydes with benzoquinones, as disclosed by G. A. Kraus et al., *J. Org. Chem.*, 57, 3256 (1992), and references cited therein. Compound 1 is fast reacted with a triflating agent such as N-phenyltrifluoromethanesulfonimide, in the presence of a base such as hydride anion, to yield bis(triflate) 2. Compound 2 is reacted with molar excess of N-methylethylenediamine in an organic solvent such as $CH_3CN$ to yield 3. N-methylethylenediamine can be replaced with other substituted diamines of general formula $R_1NHCH_2CH(R_2)NH_2$ wherein $R_1$ and $R_2$ are as defined above. When $R_2$ is OY, Y can be an acid labile protecting group such as trialkylsilyl, tetrahydrofuranyl or 1-ethoxyethoxy.

The remaining triflate group can be displaced by a number of nucleophilic functional groups to yield compounds of formula (I), followed by further conversion of the 3- or 7-substituents to other substiments of interest, e.g. by removal of the 3-hydroxy protecting group Y with dilute aqueous acid. These reactions are preferably carded out in the presence of a Pd(II) catalyst such as $PdCl_2$, palladium(II) carboxylate salts, such as $Pd(OAc)_2$, $Pd_2(dba)_3$ and $Pd(TFA)_2$, $PdSO_4$, $Pd(O_2CCF_3)_2$, $PdBr_2$, $Pd(CN)_2$, $Pd(NO_3)_2$, Pd(II) acetylacetonate and the like. Other Pd catalysts which can be used in the present method include those disclosed in Blaser et al. (U.S. Pat. No. 4,335,054) at Col. 6, line 5 to Col. 7, line 3.

For example, as shown in Scheme 1, reaction of compound 3 with cyanide anion in the presence of $Pd_2(dba)_3$ wherein dba is trans, trans-dibenzylideneacetone·$CHCl_3$ and 1,1'-bisdiphenylphosphine)fenocene (DPPF) in 1-methyl-2-pyrrolidinone (NMP), provided 7-cyano-compound 5 in 78% yield. Likewise, treatment of a solution of 3 in DMSO-methanol with $Et_3N$, $Pd(OAc)_2$, 1,3-bis(diphenylphosphine)propane (DPPP) and carbon monoxide (CO) afforded the 7-carbomethoxy compound 6. Medazepam 4 can be prepared by reaction of compound 3 with a chloride in source such as LiCl in the presence of a Pd(II) catalyst. In turn, medazepam can be converted to diazepam in satisfactory yield by known procedures. See A. M. Felix et al., *J. Het. Chem.*, 5, 731 (1968).

Compounds of Formula I above, and medicinally acceptable acid-addition salts of such compounds, are valuable therapeutic agents, being useful as anxiolytics, antidepressants, anti-alcoholism agents, muscle relaxants, sedatives, and anticonvulsants. These compounds can be administered internally, for example, parenterally or orally, and can be compounded into conventional pharmaceutical dosage forms with amounts adjusted to individual requirements, such as tablets, capsules, lozenges, suppositories, suspensions, solutions, and the like.

The invention will be further described by reference to the following detailed examples.

EXAMPLE 1

2,5-Ditrifluoromethanesulfonyloxybenzophenone (2)

NaH (60% in mineral oil, 0.95 g, 0.0237 mol) was added to a solution of 2,5-dihydroxy-benzophenone (2.30 g, 0.0107 mol) (G. A. Kraus et al., *J. Org. Chem.*, 57, 3256 (1992)) in THF (40 ml) at 0° C. and the mixture was stirred at room temperature for 0.5 hr. A solution of N-phenyltrifluoromethanesulfonimide (Aldrich Chem. Co.) in THF (40 ml) was added to the reaction mixture at −78° C. and this reaction mixture was stirred at room temperature for 2 hr. Five percent $KHSO_4$ solution (150 ml) was added to this mixture and extracted with AcOEt (100 ml×2). The organic layer was washed with $H_2O$, brine, and dried over $MgSO_4$. After evaporation of the solvent under reduced pressure, the residue was purified by flash column chromatography on silica gel (hexane:$Et_2O$=30:1 ) to give 2 as an oil (3.93 g, 76%).

EXAMPLE 2

2,3-Dihydro-1-methyl-5-phenyl-7-trifluoromethanesulfonyloxy-1H- 4-benzodiazepine (3).

A mixture of 2 (103 mg, 0.215 mmol) and N-methylethylenediamine (0.076 ml, 0.86 mmol) in acetonitrile (3 ml) was stirred at 90° C. for 9 hr. To this mixture, water (10 ml) was added and the mixture was extracted with AcOEt (10 ml×2). The organic layer was washed with $H_2O$, brine, and dried over $MgSO_4$. After evaporation of the solvent under reduced pressure, the residue was purified by flash column chromatography on silica gel ($CH_2Cl_2$:AcOEt=6:1) to give 3 as an oil (47.6 mg, 58%).

EXAMPLE 3

7-Cyano-2,3-dihydro-1-methyl-5-phenyl-1H-1,4-benzodiazepine (5)

To the dry KCN (35.5 mg, 0.55 mmol), [$Pd_2(dba)_3$]·$CHCl_3$ (3.7 mg, 0.0035 mmol), DPPF (1,1'-bis(diphenylphosphine)ferrocene) (8.0 mg, 0.0144 mmol), 3 (70 mg, 0.182 mmol), and 1-methyl-2-pyrrolidinone (0.2 ml) were added, and heated at 90° C. with stirring for 3 hr. After addition $H_2O$ (10 ml) and AcOEt (10 ml), the organic layer was separated and washed with $H_2O$, brine, and dried over $MgSO_4$. After evaporation of the solvent under reduced pressure, the residue was purified by flash column chromatography on silica gel (hexane:AcOEt=4.5) to give white crystals of 5 (37 mg, 78%), mp 151°–153° C. (from $Et_2O$-hexane) (lit. mp 149°–150° C.). (L. H. Stembach et al., *J. Org. Chem.*, 28, 3013 (1963)).

EXAMPLE 4

2,3-Dihydro-7-methoxycarbonyl-1-methyl-5-phenyl-1H-1,4-benzodiazepine (6).

$Et_3N$ (0.094 ml, 0.676 mmol) is added to a solution of i! (200 mg, 0.521 mmol) in DMSO (1.2 ml) and MeOH (1.2 ml). The catalyst, $Pd(OAc)_2$ (5.8 mg, 0.026 mmol), and 1,3-bis(diphenylphosphino)propane (DPPP) (10.7 mg, 0.026 mmol) was then added. A stream of CO was passed through the mixture for 3 min., then the flask was heated at 80° C. for 3 hr under a CO balloon. The reaction was quenched with $H_2O$ (20 ml) and extracted with AcOEt (10 ml×2). The organic layer was washed with $H_2O$, brine, and dried over MgSO₄. After evaporation of the solvent under reduced pressure, the residue was purified by flash column chromatography on silica gel (CH₂Cl₂:AcOEt=6:1 to give 6 as an oil (145 mg, 95%).

EXAMPLE 4

7-Chloro-2,3-dihydro-1-methyl-5-phenyl-1H-1,4-benzodiazepine (Medazepam) (4)

To dry LiCl (82.8 mg, 2.0 mmol), [Pd₂(dba)₃]·CHCl₃ (3.9 mg, 0.0036 mmol), DPPF (1,1'-bis(diphenylphosphine)ferrocene) (8.0 mg, 0.0144 mmol), 3 (70 mg, 0.812 mmol), and 1-methyl-2-pyrrolidionone (0.4 ml) were added. The reaction was heated at 90° C. with stirring for several hours. After the addition of water (20 ml) and ethyl acetate (40 ml), the organic layer was separated and washed with brine and dried over Na₂SO₄. After evaporation of the solvent in vacuo, the residue was purified by flash column chromatography on silica gel to give 4 as a white solid (18 mg, 39%).

EXAMPLE 5

Diazepam

A solution of 792 mg (2.7 mmoles) of IV in 10 ml of chloroform is treated at 0° with 180 ml (9.7 mmoles) of 0.054 molar solution of ruthenium tetroxide in chloroform (addition time 0.5 hour). The mixture is then stirred for 0.5 hour and 5 ml of 2-propanol and 200 ml of water is added. The mixture is filtered through Celite. The layers are separated and the aqueous layer was washed with chloroform. The combined chloroform layers are dried over magnesium sulfate, filtered and evaporated to a small volume. Hexane is added and the solution is set aside for crystallization. Filtration affords 426 mg (55%) of diazepam as white prisms.

All publications, patents and patent documents cited herein are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for preparing a compound of the formula (I):

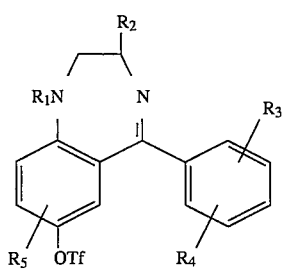

wherein $R_1$ is H or $(C_1-C_4)$alkyl, optionally substituted by $CF_3$ or $N(R)_2$ wherein each R is individually H, phenyl, or $(C_1-C_4)$alkyl, $R_2$ is H, $(C_1-C_4)$alkyl optionally substituted by $(C_1-C_4)$alkoxy, $(C_1-C_4)$alkoxycarbonyl, phenyl or OY wherein Y is $(C_1-C_4)$alkyl or an acid-labile hydroxy protecting group, $R_3$, $R_4$ and $R_5$ are individually H, halo, $(C_1-C_4)$alkoxy, nitro, $CF_3$ or $OCF_3$ and Tf is trifluoromethylsulfonyl, comprising:

(a) bis-triflating a compound of formula (II):

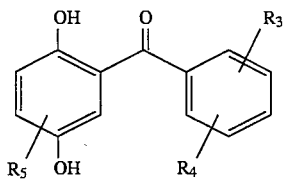

wherein $R_3$, $R_4$ and $R_5$ are as defined above, to yield a compound of formula (III):

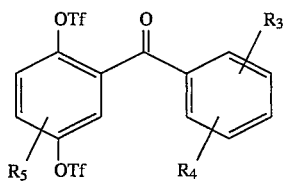

wherein $R_3$, $R_4$, $R_5$, and Tf are as defined, above; and (b) reacting compound III with a 1,2-bisaminoethane of formula (IV): $(R_1)(H)NCH_2CH(R_2)NH_2$ (IV) to yield the compound of formula (I) wherein $R_1$, $R_2$, $R_3$, $R_4$, $R_5$ and Tf are as defined above.

2. The method of claim 1, further comprising reacting the compound of formula (I) with chloride ion in the presence of a palladium catalyst to yield a compound of formula (V):

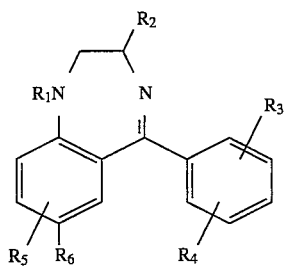

wherein $R_1-R_5$ are as defined above and $R_6$ is Cl.

3. The method of claim 1 wherein $R_1$ is $(C_1-C_4)$alkyl.
4. The method of claim 1 wherein $R_2$ is H.
5. The method of claim 1 wherein $R_3$, $R_4$ and $R_5$ are H or halo.
6. The method of claim 2 wherein $R_1$ is $CH_3$, $R_2$ is H, and $R_3$, $R_4$ and $R_5$ are H.
7. The method of claim 1 wherein the compound of formula II is triflated with N-phenyltrifluoromethanesulfonamide.
8. The method of claim 1 wherein the 1,2-bisaminoethane is N-methylethylenediamine.

* * * * *